United States Patent
Goldstein et al.

(10) Patent No.: US 6,881,382 B2
(45) Date of Patent: Apr. 19, 2005

(54) FRAGRANCE SIGNALING OF AN EVENT

(75) Inventors: Richard A. Goldstein, New York, NY (US); Clint Dee Winton Brooks, Sea Bright, NJ (US); Lewis Michael Popplewell, Morganville, NJ (US); Donald W. Buchanan, Jr., Middletown, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 452 days.

(21) Appl. No.: 10/114,414

(22) Filed: Apr. 2, 2002

(65) Prior Publication Data

US 2003/0185716 A1 Oct. 2, 2003

(51) Int. Cl.[7] .............................. A61L 9/03; A61L 9/12
(52) U.S. Cl. ....................... 422/123; 422/124; 422/125; 116/200; 429/178
(58) Field of Search ................................ 422/125, 305, 422/306, 123, 124, 5; 116/200, 201, 208; 429/178

(56) References Cited

U.S. PATENT DOCUMENTS

| | | | |
|---|---|---|---|
| 4,534,891 A | 8/1985 | Boden et al. |
| 5,311,877 A | 5/1994 | Kishi |
| 5,642,092 A | 6/1997 | Dunne et al. |
| 6,239,857 B1 | 5/2001 | Wittek |
| 6,244,987 B1 | 6/2001 | Ohsuga et al. |
| 6,282,458 B1 | 8/2001 | Murayama et al. |

FOREIGN PATENT DOCUMENTS

| | | | |
|---|---|---|---|
| JP | 2003304645 A | * | 10/2003 |
| KR | 2001078935 A | * | 8/2001 |

* cited by examiner

Primary Examiner—E. Leigh McKane
(74) Attorney, Agent, or Firm—Joseph F. Leightner

(57) ABSTRACT

Apparatus and methods for signaling an event using fragrance are disclosed. A fragrance emitting device is activated to a low battery voltage indicator in an electronic device, serving as a warning to replace the battery, either in place of or complimentary to conventional indicators such as warning lights or audible signals. The fragrance emitting system can be integrated into the electronic device itself or can be part of the battery.

19 Claims, 1 Drawing Sheet

FRAGRANCE SIGNALING OF AN EVENT

FIELD OF THE INVENTION

The present invention relates to methods and apparatus for using fragrance to signal an event.

BACKGROUND OF THE INVENTION

Fragrance signaling has many uses and potential benefits, for example, fragrance can be dispersed to enhance an environment. Fragrance can also be used to signal unsafe conditions for the hearing or visually impaired.

There are numerous systems that utilize electromechanical devices to dispense fragrance into an environment. For example, U.S. Pat. No. 6,282,458, issued to Murayama, et al., the contents of which are incorporated by reference, discloses a system for releasing fragrance into an environment based on feedback from sensors that measure the environment into which the fragrance is released. The feedback results in the fragrance being emitted so as to give the impression of directionality. U.S. Pat. No. 6,244,987 issued to Ohsuga; et al., the contents incorporated by reference, discloses a virtual reality environment adapted for use with exercise equipment that releases fragrance according to the performance of the exercise as the user "moves" through the virtual reality environment. Similarly, U.S. Pat. No. 6,239,857 issued to Wittek, the contents incorporated by reference, discloses a device for adding fragrance to an environment synchronized with an audiovisual presentation.

It is also known to use fragrance for safety purposes. For example, Nissan Motors has proposed a system in which a camera detects vehicle operator drowsiness and uses the release of a stimulating fragrance to warn and combat the drowsiness. This system is disclosed, for example in the Nov. 1, 1995 edition of the Detroit News in an article entitled "The Science of Crash Avoidance" and in U.S. Pat. No. 5,311,877 issued to Kishi and incorporated by reference. Another example of using fragrance to avoid danger is U.S. Pat. No. 5,642,092 issued to Dunne, et al. and incorporated by reference, which discloses an evacuation assistance system that is triggered by a signal from a smoke detector to create a "trail" of a fragrance to direct occupants of a building to an exit.

Numerous safety devices and devices of a critical nature operate on battery power. Often, the battery life is variable and cannot be judged by time alone or by performance. Existing devices often have low battery warning lights or available alarms, but these are often overlooked in environments full of noise and distractions. Thus, there exists a long felt and as of yet unmet need to provide additional indicators of unsafe conditions and indications of low battery voltage in particular.

SUMMARY OF THE INVENTION

The present invention provides apparatus for emitting a fragrance that is connected to a battery, wherein a fragrance is emitted when a predetermined voltage level occurs in the battery. Either a voltage is monitored and the mechanism automatically emits fragrance when a voltage below said predetermined value occurs, or the mechanism automatically emits fragrance when a voltage below said predetermined value is created by activating a testing circuit. Preferably, the apparatus and one or more batteries are constructed as a modular unit separable from a device being supplied with power by said batteries. In certain embodiments, a fragrance is sealed within a polymer that has a porosity that varies as a function of an electrical current flowing through the polymer, whereby upon detection of a voltage below a predetermined level, the polymer releases a fragrance.

In other embodiments, a chemical osmotic pump is provided and the pump is triggered to produce a fragrance upon detection of a voltage below a predetermined level, the polymer releases a fragrance. In certain embodiments of the present invention, the battery is disposable, however, in other embodiments, the battery is rechargeable. In any of the apparatus contemplated herein, the fragrance is comprised of at least one constituent having a low threshold of detectability and a low dosage requirement and is preferably provided in the form of either a fragranced polymer, gel, or a sponge into which fragrance has been absorbed.

In other embodiments, the present invention provides improvements to devices that have a voltage monitor and a battery by providing a fragrance emitting device comprising a trigger circuit connected to said voltage monitor. In certain preferred embodiments, the low battery detection circuit in the device creates a low battery warning signal that is connected to a first warning stimulus device, such as a horn, and this same warning signal is connected to a fragrance diffusion device so that the fragrance is emitted upon the same condition that would trigger the first stimulus device. In certain preferred embodiments, the fragrance diffusion device is a chamber that is opened to the environment, which may include a solenoid valve.

In certain other preferred embodiments, a melt polymer is provided that releases fragrance by vaporization due to the addition of heat, the heat may be from a heater element that converts electrical current to heat or that converts friction to heat. The fragrance itself may diffuse naturally or be driven by a fan.

In an additional embodiment, a battery terminal is provided that erodes, and when eroded to a certain point a polymer, gel or sponge containing a fragrance will be exposed, thus emitting fragrance after a predetermined time.

DETAILED DESCRIPTION OF THE PREFERRED EMBODIMENTS

Figures 1A, 1B:
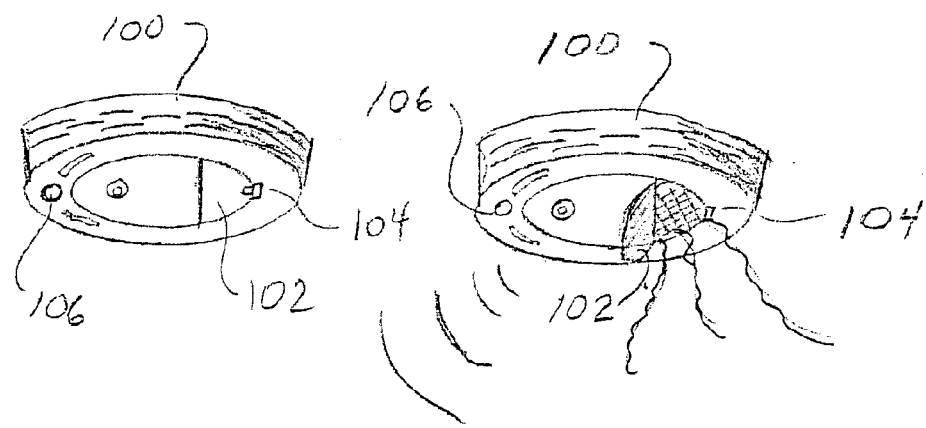
FIGS. 1A–1B is a perspective view of a smoke detector made in accordance with the present invention.

In a first embodiment of the present invention apparatus integrated with a battery or apparatus connected to the battery emits a fragrance via an integral mechanism, either automatically when voltage drops below a predetermined value, or alternatively when tested by the end user. This embodiment may be implemented in a variety of situations, for example in devices where the battery is at least somewhat exposed or accessible for testing. This embodiment is most useful in devices that are low cost and is also particularly useful in devices where the battery itself is physically relatively large. In these embodiments, modular or external batteries are typically supplied.

There are a number of methodologies by which the first embodiment of the present invention can be implemented. A terminal that is designed to erode can be used and when eroded to a certain point a polymer, gel or sponge containing a fragrance will be exposed, thus emitting fragrance after a predetermined time.

Additionally, batteries can be constructed that contain a reservoir that is triggered to produce a fragrance as the battery fails. In such embodiments, a consumer would "test" a suspect battery by squeezing the battery to complete a circuit. A low voltage condition results in fragrance being emitted, whereas if the voltage was sufficiently high, the pump would not be activated or alternatively the release of fragrance via a valve would not occur. Representative examples of goods in which this first embodiment of the present invention would find use are flashlights, toys, automobile batteries, storage batteries and batteries used in cordless and cellular phones.

In the embodiments described immediately above, the characteristics of the fragrance implemented would preferably be that they are very odor active, i.e., having a low threshold of detectability and a low dosage requirement, that the fragrance be distinctive and that it not easily absorbed, particularly into plastics since in low cost environments the fragrance will be housed in or impregnated in a plastic housing. Finally, in these embodiments the fragrance will not be substantive.

In a second class of embodiment, a fragrance emitting device is triggered by voltage monitors similar to those currently built into many electronics. These embodiments of the present invention will find particular applicability in devices where the battery is enclosed, or in devices where the battery is rechargeable. Additionally, these embodiments of the present invention will find particular applicability in devices that can bear an incremental cost, in other words relatively expensive devices with high residual value that can absorb or justify the minor expense involved with adding the improvements of the present invention. In such embodiments, the devices will typically have existing low battery detection circuits that create a low battery warning signal.

In embodiments made in accordance with this aspect of the present invention, the existing warning stimulus, e.g., sound or light would be replaced or augmented by the diffusion of a fragrance. This is preferably accomplished using a fragranced polymer, gel, or a sponge into which fragrance has been absorbed. The fragrance is emitted in these embodiments by the action of a door, a solenoid valve, a melt polymer, by vaporization due to the addition of heat, or by the action of a fan. Alternatively, the fragrance can be activated by the heat created by friction or by conversion of electrical current, and such systems are designed so that when there is a voltage drop it triggers the generation of heat, which in turn causes the fragrance to be emitted. Finally, a third implementation of this embodiment of the present invention is to provide a mechanical mechanism to eject or expose fragrance upon the receipt of an electrical signal. For example, the signal that trips the alarm horn in a smoke detector (either due to fire or due to a low battery) could also cause a ribbon of fragrance containing polymer to drop down and suffuse fragrance into the space below.

These embodiments of the present invention will find use, for example, in camcorders, portable music equipment, computers and smoke detectors. As explained above, the fragrance chemicals will be low threshold/low dosage, distinctive and substantive. However, in these embodiments, the fragrance may also be replaced, changed or otherwise selected.

The specific example of detecting and signaling low battery voltage occurs in an electronic device by the emission of fragrance to indicate potential loss of power or the need to replace the battery can either be in place of or complementing commonly used visual and/or auditory signals of low batteries. As explained above there are at least two fundamentally different ways to implement the invention, either incorporating the signal as part of the battery itself, or as part of the device which the battery powers. Each has specific benefits and preferred scenarios for use.

In any embodiment, the fragrance may be comprised of any chemical, or chemical mixture with an aroma. Obviously, those chemicals/mixtures which provide an aroma suitable for the situation are preferred. For example, signaling a low battery condition in a smoke detector may be best served via release of an unpleasant, diffusive smell. The manner of retaining the fragrance prior to release can similarly be varied to fit the specific situation. Modes of retention and delivery that may be used include: liquid mixtures, absorption of fragrance on carriers such as silica, providing a matrix of fragrance with suitable polymers, using natural products that contain aromatics (e.g., spices), and creating semisolid gels such as those used as air fresheners. What is important is that the fragrance be stabilized prior to release, and that once release is triggered an appropriate quantity of fragrance can be emitted so that the signal is perceived.

Many types of fragrances can be employed in the present invention, the only limitation being the compatibility with the other components being employed in the invention, such as a polymer or carrier.

Preferably fragrance which is employed in the device should be distinctive, such that a person in the vicinity will recognize an uncommon fragrance in the area. The fragrance may be formulated to be pleasant or unpleasant thereby providing a signal to the person. The fragrance may be comprised of a single chemical or a mixture of two or more fragrances.

Suitable pleasant fragrances include but are not limited to fruits such as almond, apple, cherry, grape, pear, pineapple, orange, strawberry, raspberry; musk, leaf alcohol which is often described as the cut-grass smell; flower scents such as lavender-like, rose-like, iris-like, and carnation-like. Other pleasant scents include herbal scents and woodland scents derived from pine, spruce and other forest smells. Fragrances may also be derived from various oils, such as essential oils, or from plant materials such as peppermint, spearmint and the like.

Fragrance chemicals that provide unpleasant odors that can be employed in the present invention include, but are not limited to, mercaptans such as $H_2S$; styrene, phenolics and amines such as ammonia.

A list of suitable fragrances is provided in U.S. Pat. No. 4,534,891, the contents of which are incorporated by reference as if set forth in their entirety. Another source of suitable fragrances is found in *Perfumes Cosmetics and Soaps*, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

Olfactory effective amount is understood to mean the amount of compound in perfume compositions the individual component will contribute its particular olfactory characteristics, but the olfactory effect of the perfume composition will be the sum of the effects of each of the perfume or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of fragrance of the invention employed in the article varies depending on the intensity of the odor desired and the chemicals employed to produce the fragrance. Many fragrance chemicals have odor thresholds of less than 500 parts per million, commonly less than 100 parts per million. Some fragrance ingredients have odor thresholds in the parts per billion range. Preferably the fragrance chemicals when signaling a low voltage situation of less than 500 parts per billion, more generally from about 50 to about 250 parts per billion. Well known materials such as surfactants, emulsifiers, can also be employed with the fragrance without departing from the scope of the present invention.

Those with skill in the art will be able to employ the desired level of the compounds of the invention to provide the desired fragrance and intensity.

Modes of achieving release once a low battery condition is achieved may also be varied. For example, one mode of release is that a low voltage condition triggers a door or valve to open; thus allowing fragrance held in a reservoir as either a liquid or gel to diffuse into the environment. Another mode of release could be that a low voltage condition triggers heating of a solid fragrance-polymer sheet, thus promoting diffusion of the fragrance. Those of skill in the art will appreciate that the release may be triggered automatically, i.e., once a set low voltage is achieved or manually, i.e., when a battery or device is tested for low voltage.

Referring first to FIG. 1A, there is shown a smoke detector or similar device that is well known in the art. In accordance with the present invention, the smoke detector 100 is modified to include a hinged door 102 held in place by a solenoid a-activated latch 104. FIG. 1B illustrates the condition of the smoke detector 100 upon the occurrence of either a fire or a low battery condition. In either event, the smoke detector 100 already includes circuitry that sends a signal to an audible alarm circuit. However, in accordance with the present invention, this same signal also triggers the solenoid latch 104 to open and thereby exposes a portion of the housing such that a fragrance may emanate, either naturally by convection or by forced vaporization, as explained herein. It should be noted that there are useful embodiments wherein the fragrance is emitted only during a low battery warning, or, alternatively, wherein the fragrance is emitted only during a fire, or both.

Figure 2:
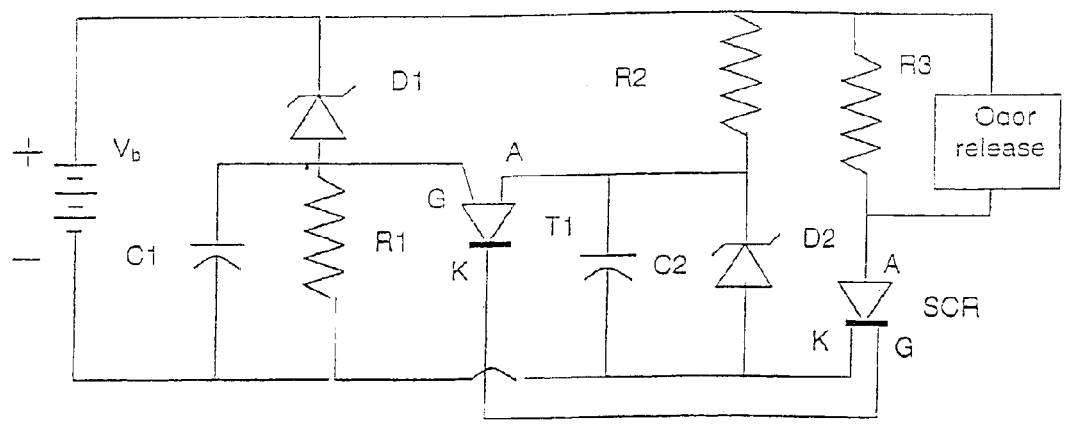
FIG. 2 is a schematic of a circuit used to signal an event.

Referring now to FIG. 2, a low-battery signaling circuit is illustrated. It should be understood that depending on the actual application, many methods of delivering a fragrance signal may be used and the specific embodiment disclosed herein is for purposes of illustration only. The circuit shown on FIG. 2 and the fragrance-signaling device that uses it are useful in any product that is powered by a battery and is particularly useful for inexpensive portable devices that lack space to incorporate a visual or audible signaling.

In FIG. 2, $V_b$ is the battery powering a device. Attached in parallel to this battery is a circuit that releases a fragrance when Vb drops below 6.0 vdc. The battery voltage $V_b$ when fresh is 9.0 vdc. Value for R1 is 1000 Ω, value for R2 is 1 MΩ. Zener diodes are reversed biased and Zener voltages are set D1=5.5 vdc and D2=6 vdc. It is assumed that each zener diode has an internal resistance of 20 Ω. Transistor T1 is a reversed bias p-channel MOSFET with a threshold voltage of 0.1 vdc. In operation, the Zener diode D2 set the T1 anode voltage at 6 vdc taking a voltage drop of 3 v through R2 (drawing 3 μA) Zener diode D1 is set a 5.5 vdc. For a new battery voltage on the gate of T1 is set at 8.8 v. Since the voltage on the gate is higher than on the anode, no current flows from the anode to cathode of T1. Table 1 shows the progression of the events as the battery ages:

TABLE 1

| Battery Voltage, $V_b$ | Gate Voltage, $V_G$ | Anode Voltage, $V_A$ | T1 Bias Voltage $V_A - V_G$ |
|---|---|---|---|
| 9.0 | 8.82 | 6.0 | −2.82 |
| 8.0 | 7.84 | 6.0 | −1.84 |
| 7.0 | 6.89 | 6.0 | −0.86 |
| 6.0 | 5.89 | 6.0 | +0.11 |

Since T1 bias voltage is now greater than the T1 threshold voltage, transistor T1 begins to conduct. Capacitor C2, which was charged to 6 vdc discharges current through T1 to the silicon-controlled relay (SCR). The SCR pulls in contacts that connect the battery across the fragrance releasing device (e.g., polymer-fragrance sheet heated, solenoid door opens releasing fragrance). The odor is perceived by the user, who then is warned that the battery charge is low.

Finally, short distance communications such as Bluetooth or IEEE 802.11b become more widespread, it is envisioned that a fragrance signaling device such as shown above could be incorporated in something wearable, such as a watch. Household electronic devices could then "talk to" this wearable device and trigger a fragrance release. This would alert the wearer that an electronic device in the vicinity had a battery that was near exhaustion.

The present invention has been discussed in terms of certain preferred embodiments. Those of skill in the art will recognize that various modifications may be made to the specific embodiments disclosed herein without departing from the scope of the invention. Although discussed primarily in terms of emitting a fragrance upon a low voltage condition in a battery, it should be understood that the present invention is useful in other contexts and with a wide variety of electromechanical and electronic systems that might not be considered battery operated. Moreover, while certain features may be shown or discussed in relation to a particular embodiment, such individual features may be used on the various other embodiments of the invention. Thus, there are numerous alternatives, modifications, adaptations beyond those disclosed which still incorporate the spirit of the invention. In order to apprehend the full scope of the present invention, reference should be made to the appended claims.

What is claimed is:

1. Apparatus for emitting a fragrance connected to a battery, wherein a fragrance is emitted when a predetermined voltage level occurs in the battery.

2. The apparatus of claim 1 wherein further comprising a voltage monitor wherein a mechanism automatically emits fragrance when said voltage monitor detects a voltage below said predetermined value.

3. The apparatus of claim 1 further comprising a testing circuit and wherein a mechanism automatically emits fragrance when a voltage below said predetermined value is created by activating said testing circuit.

4. The apparatus of claim 1 wherein the apparatus and one or more batteries are constructed as a modular unit separable from a device being supplied with power by said batteries.

5. The apparatus of claim 1 further comprising a fragrance sealed within a polymer wherein the polymer has a porosity that varies as a function of an electrical current flowing through the polymer, whereby upon detection of a voltage below a predetermined level, the polymer releases a fragrance.

6. The apparatus of claim 1, wherein the battery is rechargeable.

7. The apparatus of claim 1, wherein the fragrance is comprised of at least one constituent having a low threshold of detectability and a low dosage requirement.

8. The apparatus of claim 7 wherein the constituent is chosen from the group consisting of: a fragranced polymer, gel, or a sponge into which fragrance has been absorbed.

9. In a device comprising a voltage monitor and a battery, the improvement comprises providing a fragrance emitting device comprising a trigger circuit connected to said voltage monitor.

10. The device of claim 9 wherein a low battery detection circuit that creates a low battery warning signal is connected to a first warning stimulus device, and wherein said warning signal is connected to a fragrance diffusion device.

11. The apparatus of claim 10 wherein the fragrance diffusion device comprises a chamber that is opened to the environment.

12. The apparatus of claim 10 wherein the fragrance diffusion device comprises a solenoid valve.

13. The apparatus of claim 10 wherein the fragrance diffusion device comprises a melt polymer that releases fragrance by vaporization due to the addition of heat.

14. The apparatus of claim 13, further comprising a heater element that converts electrical current to heat.

15. The apparatus of claim 13, further comprising a heater element that converts friction to heat.

16. The apparatus of claim 10 further comprising a fan for diffusing a fragrance.

17. The apparatus of claim 10 further comprising a mechanical mechanism to expose fragrance upon the receipt of an electrical signal.

18. The apparatus of claim 17 wherein the warning signal activates a mechanism whereby a ribbon of fragrance containing polymer drops down and suffuses fragrance into a space below.

19. A battery terminal comprised of an erodable portion overlying a fragrance layer containing a fragrance wherein the erodable layer erodes and exposes the fragrance, thereby emitting fragrance after a predetermined time.

* * * * *